(12) United States Patent
Ternes et al.

(10) Patent No.: US 9,393,429 B2
(45) Date of Patent: Jul. 19, 2016

(54) PROGRAMMING AMBULATORY OPTIMIZATION SYSTEMS AND METHODS FOR CARDIAC RHYTHM MANAGEMENT

(75) Inventors: David J. Ternes, Roseville, MN (US); Keith L. Herrmann, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 442 days.

(21) Appl. No.: 13/083,961

(22) Filed: Apr. 11, 2011

(65) Prior Publication Data

US 2011/0282409 A1 Nov. 17, 2011

Related U.S. Application Data

(60) Provisional application No. 61/333,935, filed on May 12, 2010.

(51) Int. Cl.
| | |
|---|---|
| *A61N 1/05* | (2006.01) |
| *A61N 1/372* | (2006.01) |
| *A61N 1/368* | (2006.01) |

(52) U.S. Cl.
CPC ............ *A61N 1/37247* (2013.01); *A61N 1/368* (2013.01); *A61N 1/3682* (2013.01); *A61N 1/3684* (2013.01)

(58) Field of Classification Search
CPC ............................ A61N 1/3682; A61N 1/3622
USPC ....................................................... 607/9, 11
See application file for complete search history.

(56) References Cited

U.S. PATENT DOCUMENTS

| | | |
|---|---|---|
| 6,289,248 B1 | 9/2001 | Conley et al. |
| 6,542,775 B2 | 4/2003 | Ding et al. |
| 6,597,951 B2 | 7/2003 | Kramer et al. |
| 6,622,040 B2 | 9/2003 | Ding et al. |
| 6,684,103 B2 | 1/2004 | Ding et al. |
| 6,690,972 B2 | 2/2004 | Conley et al. |
| 6,856,836 B2 | 2/2005 | Ding et al. |
| 6,859,665 B2 | 2/2005 | Ding et al. |
| 6,915,160 B2 | 7/2005 | Auricchio et al. |
| 6,961,616 B2 | 11/2005 | Kramer et al. |
| 6,999,815 B2 | 2/2006 | Ding et al. |
| 7,010,349 B2 | 3/2006 | Conley et al. |

(Continued)

*Primary Examiner* — Christopher D Koharski
*Assistant Examiner* — Michael D Abreu
(74) *Attorney, Agent, or Firm* — Pauly, DeVries Smith & Deffner, LLC (57) ABSTRACT

A system and method for cardiac rhythm management using a programmable cardiac rhythm management device is described, wherein the method includes storing parameter interaction constraints between different programmable parameters, storing programmable parameters for the device, wherein each programmable parameter has a predefined set of possible values, wherein one programmable parameter is a delay value, and calculating initial seed values for user-set delay range input fields, wherein the seed values do not violate any parameter interaction constraints and maximize the difference between ends of the user-set delay range, wherein the user-set delay range provides the outer limits of a programmed delay value. The method further includes presenting an input screen to the user on a user display device, wherein the input screen comprises user-set delay range input fields containing the initial seed values. The method further includes receiving values from a user for the user-set delay range, collecting patient data including ambulatory patient data, and determining a recommended delay value based on the ambulatory patient data.

15 Claims, 9 Drawing Sheets

(56) References Cited

U.S. PATENT DOCUMENTS

| | | |
|---|---|---|
| 7,013,176 B2 | 3/2006 | Ding et al. |
| 7,110,817 B2 | 9/2006 | Yu et al. |
| 7,123,960 B2 | 10/2006 | Ding et al. |
| 7,158,830 B2 | 1/2007 | Yu et al. |
| 7,184,835 B2 | 2/2007 | Kramer et al. |
| 7,203,540 B2 | 4/2007 | Ding et al. |
| 7,231,248 B2 * | 6/2007 | Kramer et al. .......... 607/9 |
| 7,310,554 B2 | 12/2007 | Kramer et al. |
| 7,613,672 B2 | 11/2009 | West et al. |
| 2011/0202099 A1 * | 8/2011 | Makdissi .......... 607/4 |

\* cited by examiner

FIG. 1

SETTINGS - NORMAL BRADY / CRT  — 140
⤺ CLOSE

PARAMETERS

| | | | PACING AND SENSING |
|---|---|---|---|
| MODE | DDDR | | AMPLITUDE  PULSE WIDTH  SENSITIVITY |
| LOWER RATE LIMIT | 60 ppm | | ○ A        [0.5] V @ [0.4] ms   [AGC 0.25] mV |
| MAXIMUM TRACKING RATE | 120 ppm | | ☐ RV      [3.5] V @ [0.4] ms   [AGC 0.25] mV |
| MAXIMUM SENSOR RATE | 120 ppm | | ◇ LV      [3.5] V @ [0.4] ms   [AGC 1.5] mV |
| PACED AV DELAY | 180 - [180] ms | | LEADS |
| SENSED AV DELAY | 120 - [120] ms | | ○ A   PACE / SENSE |
| A-REFRACTORY (PVARP) | 240 - [250] ms | | ⊕ ☐ RV  PACE / SENSE            BIPOLAR |
| RV-REFRACTORY (RVRP) | 240 - [250] ms | | ◇ LV   PACE / SENSE            BIPOLAR |
| LV-REFRACTORY (LVRP) | [250] ms | | SENSORS AND TRENDING        LVTIP>>LVRING |
| VENTRICULAR PACING CHAMBER | BiV | | |
| LV OFFSET | [0] ms | | ⊕ ACCELEROMETER   ON    ⊕ SENSOR TRENDING |
| | ⊕ SMARTDELAY™ OPTIMIZATION | | |
| 142 ⤴ | | | |

⊕ TIMING,
RATE ENHANCEMENTS,
MAGNET, NOISE

SMARTDELAY™ OPTIMIZATION

↶ CLOSE

REVIEW SUGGESTED SETTINGS — 404

PACED AV DELAY       120 ms
SENSED AV DELAY       90 ms
PACING CHAMBER        BiV
LV OFFSET              0 ms

COPY SUGGESTED SETTINGS

START MANUAL TEST  [↶] START TEST

THIS TEST WILL TEMPORARILY ALTER CRT TO ALLOW MEASUREMENT OF THE CONDUCTION DELAY FROM ATRIAL SENSES TO RIGHT AND LEFT VENTRICULAR SENSES FOLLOWED BY MEASUREMENT OF THE INTRINSIC DELAY FROM ATRIAL PACES TO RIGHT AND LEFT VENTRICULAR SENSES

USER DEFINED LIMITS FOR RANGE OF AMBULATORY SMARTDELAY™

414 — ☐ FIXED AV DELAY
        AV DELAY RANGE   424
                         120ms -  100 ms — 422
                                  250 ms — 420

416 — [OFF] AUTO SMARTDELAY™ OPTIMIZATION

DYNAMIC AV DELAY WILL BE MAINTAINED. SMARTDELAY RECOMMENDS MAXIMUM AV DELAY (LRL). THE MINIMUM AV DELAY (MSR, MTR) WILL REMAIN UNCHANGED UNLESS THE RECOMMENDED AV DELAY IS LESS THAN THAT CURRENTLY PROGRAMMED

| UTILITIES | REPORTS | INTERROGATE | VIEW CHANGES | PROGRAM | INTERACTIONS | END SESSI |

PROGRAMMING AMBULATORY OPTIMIZATION SYSTEMS AND METHODS FOR CARDIAC RHYTHM MANAGEMENT

This application claims the benefit of U.S. Provisional Application No. 61/333,935, filed May 12, 2010, the contents of which is herein incorporated by reference.

TECHNICAL FIELD

This disclosure relates generally to medical systems and, more particularly, to medical systems that can be used to communicate with and program implanted medical devices.

SUMMARY OF THE INVENTION

Embodiments of the invention are related to medical systems and methods that can be used to program, communicate with, and collect information from implanted medical devices, amongst other things.

In one embodiment, a cardiac rhythm management system includes a programmable cardiac rhythm management device having data collection devices for collecting ambulatory patient data, where the system includes a programming parameter module for storing programmable parameters for the device, wherein each parameter has a predefined set of possible values, wherein one programmable parameter is a delay value. The system further includes an optimization module adapted to optimize pace timing and determine a recommended delay value based on the ambulatory patient data, a parameter interaction module adapted for storing parameter interaction constraints between different programmable parameters, a user input device adapted to receive values from a user for a user-set delay range, wherein the user-set delay range provides outer limits of a programmed delay value, and a user display device adapted to present an input screen to the user, wherein the input screen comprises user-set delay range input fields. The system further includes seeding module adapted to calculate initial seed values for the user-set delay range input fields, wherein the seed values do not violate any parameter interaction constraints and maximize the difference between ends of the user-set delay range.

In another embodiment, a method for cardiac rhythm management using a programmable cardiac rhythm management device is described, wherein the method includes storing parameter interaction constraints between different programmable parameters, storing programmable parameters for the device, wherein each programmable parameter has a predefined set of possible values, wherein one programmable parameter is a delay value, and calculating initial seed values for user-set delay range input fields, wherein the seed values do not violate any parameter interaction constraints and maximize the difference between ends of the user-set delay range, wherein the user-set delay range provides the outer limits of a programmed delay value. The method further includes presenting an input screen to the user on a user display device, wherein the input screen comprises user-set delay range input fields containing the initial seed values. The method further includes receiving values from a user for the user-set delay range, collecting patient data including ambulatory patient data, and determining a recommended delay value based on the ambulatory patient data.

In yet another embodiment, a cardiac rhythm management system includes a programmable cardiac rhythm management (CRM) device, wherein the CRM device includes data collection devices for collecting patient data including ambulatory patient data, an ambulatory pace timing optimization module adapted to determine a recommended delay value based on the ambulatory patient data, and a programming parameter module for storing programmable parameters for the device wherein each parameter has a predefined set of possible values, wherein one programmable parameter is a delay value. The system further comprises an external programmer including control circuitry and a wireless communications module for sending instructions wirelessly to the CRM device, the programmer further including a parameter interaction module for storing parameter interaction constraints between different programmable parameters, and a user input device adapted to receive values from a user for a user-set delay range, wherein the user-set delay range provides the outer limits of a programmed delay value, wherein the user set delay range comprises a user-set maximum delay and a user-set minimum delay. The programmer further includes a user display device adapted to present an input screen to the user, wherein the input screen comprises user-set delay range input fields and a seeding module adapted to calculate initial seed values for the user-set delay range input fields, wherein a seed value for the user-set maximum delay is the highest of the predefined set of possible values that does not violate any parameter interaction constraints. Also, a seed value for the user-set minimum delay is the lowest of the predefined set of possible values that does not violate any parameter interaction constraints.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

This disclosure relates generally to cardiac rhythm management devices and, more particularly, to systems that include both a cardiac rhythm management device and an external programmer device. In particular, this disclosure relates to systems and methods for optimizing pace timing parameters and presenting the complex optimization choices to the user who will program the device.

Cardiac rhythm management (CRM) systems often include, among other things, pacers which deliver timed sequences of low energy electrical stimuli, called pace pulses, to the heart, such as via an intravascular lead wire or catheter (referred to as a "lead") having one of more electrodes disposed in or about the heart. CRM systems may also include defibrillators that are capable of delivering higher energy electrical stimuli to the heart. CRM systems may also include cardiac resynchronization therapy (CRT) devices for coordinating the spatial nature of heart depolarizations for improving pumping efficiency. For example, a device may deliver appropriately timed pace pulses to different locations of the same heart chamber to better coordinate the contraction of that heart chamber, or the device may deliver appropriately timed pace pulses to different heart chambers to improve the manner in which these different heart chambers contract together.

Figure 1:
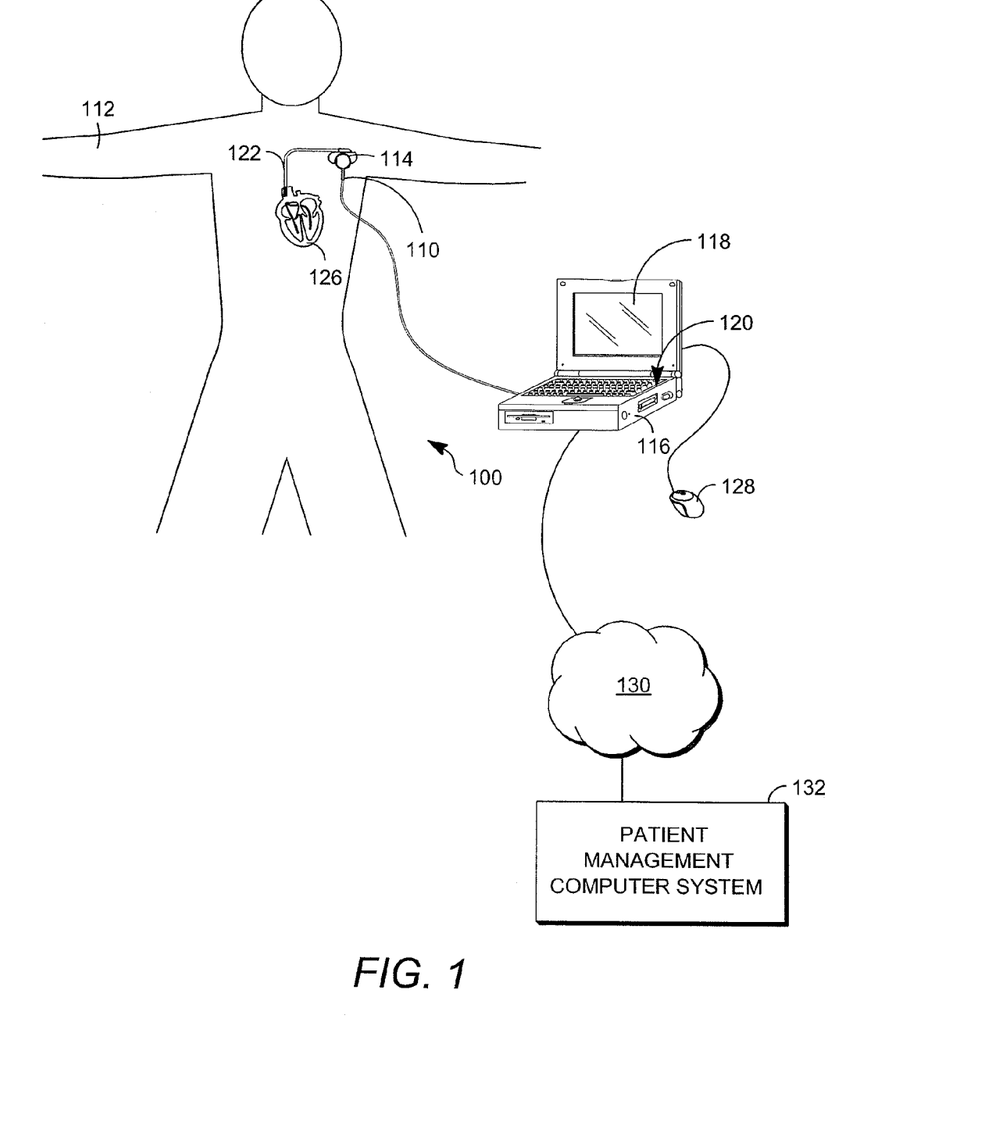
FIG. 1 is a schematic diagram of an exemplary implementation of a cardiac rhythm management (CRM) system, including an implanted CRM device, an external interface device, and a patient management computer system, consistent with at least one embodiment of the invention.

In addition to pacers, CRT devices, and defibrillators, CRM systems also include devices that combine these functions, as well as monitors and other implantable or external systems or devices for diagnosing or treating the heart. CRM systems often include external local or remote user interfaces (sometimes referred to as "programmers" or "patient management systems") for programming parameters (constraints) of an implantable cardiac rhythm management device or receiving data transmitted from the implantable cardiac rhythm management device. FIG. 1 illustrates one example of a CRM system, showing a patient 112 having an implantable medical device 114. A programmer 116 is also included in the system 100 for receiving user input and interfacing with the implantable device 114, and includes a display device 118 and a wand 110. The CRM system embodiment 100 of FIG. 1 and its additional components will be discussed in further detail herein.

Figure 2:
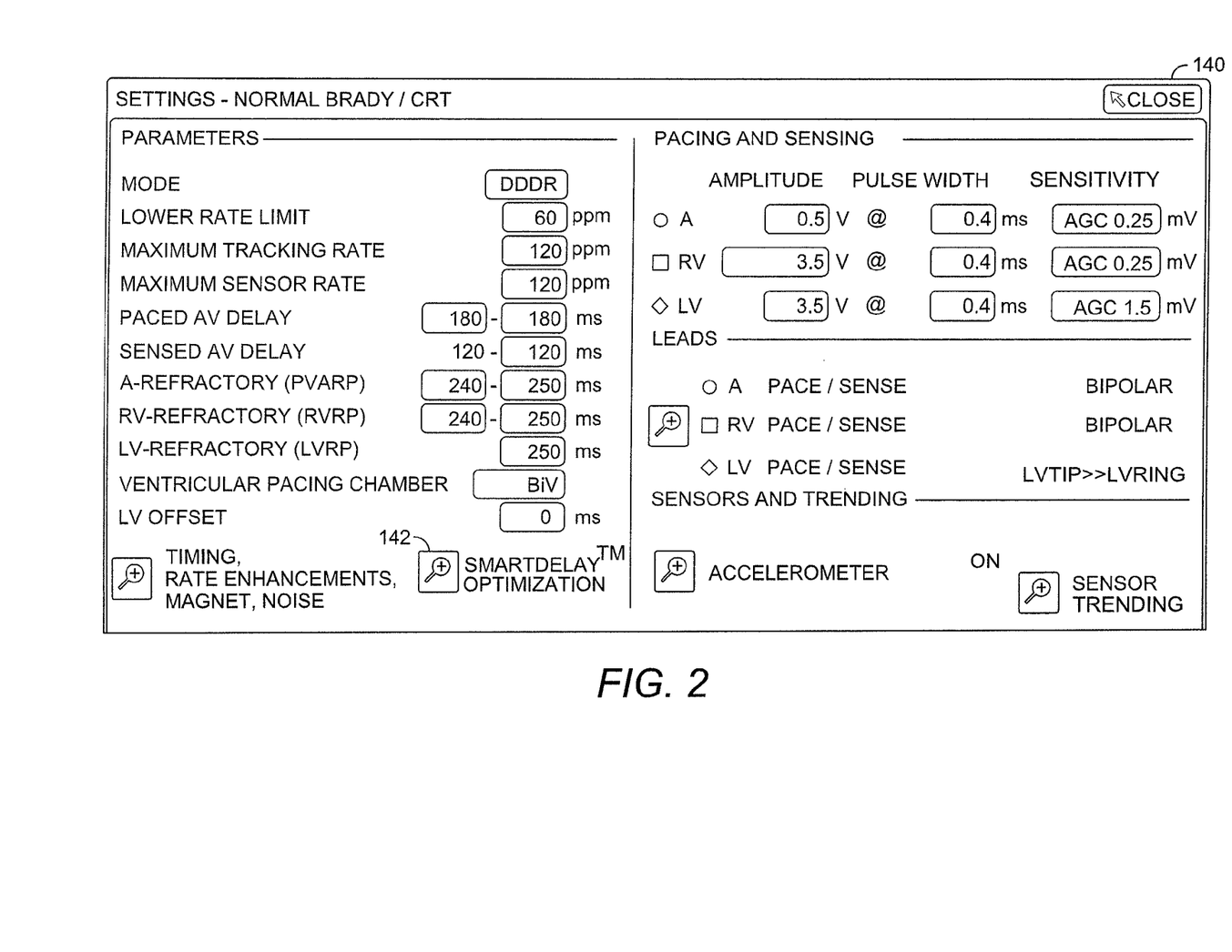
FIG. 2 is a schematic illustration of a user interface screen in accordance with various embodiments herein for programming parameters for a CRM device.

One challenge faced by users of CRM systems is in understanding and choosing the many different parameters, in order to tailor the therapy delivered to the needs of the particular patient being treated by that device. FIG. 2 is a schematic illustration of a user interface screen 140 in accordance with various embodiments herein for programming parameters for Brady and CRT settings for a CRM device. The screen includes fields for the pacing mode, the lower rate limit (LRL), the maximum tracking rate (MTR), the maximum sensor rate, the paced AV delay, the sensed AV delay and the post-ventricular atrial refractory period (PVARP), among other parameters. Typically, each programming parameter has a predefined set of possible values and the user can select one of the possible values by clicking on a field associated with that value, which causes a list of the predefined set of possible values to appear.

Adding to the complexity, the programmable parameters may interact with each other. For example, programming a first parameter to a particular value may limit the range of particular values to which a second parameter may be programmed. Because of these interactions between different programmable parameters, a complex set of constraints typically governs how the set of parameters may be programmed. Consequently, a physician faces a daunting task in programming the whole set of parameters to self-consistent values.

One of the features that requires programming in many current CRM devices is a pace timing optimization feature, which is also referred to as a pace timing optimization module or system, which provides a procedure to determine the optimal AV delay, or other optimal timing parameters, for maximizing cardiac performance indices such as left ventricular contractility, left ventricular filling, and others. One example is global left ventricular contractility, which is increased when the ventricles achieve both sufficient filling and synchronous muscle contractions, which can be accomplished via proper stimulation timing. This optimization strategy is based on clinical studies that identified a high correlation between the intrinsic conduction intervals and the optimal AV delay for maximizing left ventricular contractility. The optimal AV delay was defined as the delay that maximizes left ventricular contractility. Data gathered from intrinsic timing measurements from atrial senses and atrial paces to right and left ventricular senses is used by these optimization modules. Commonly-owned U.S. Pat. No. 6,961,616 describes aspects of one such optimization module, and is hereby incorporated by reference herein in its entirety. However, other optimization strategies may be incorporated to this system to maximize cardiac performance. In addition, there are many other patient parameters for which optimal values can be determined besides AV delay to improve cardiac performance.

One example of an optimization process and module can be referred to as commanded optimization. During a commanded optimization, the patient is in the presence of a programmer device and a clinician trained in using the system. The clinician activates the optimization module, the module gathers data from the patient, and within a few minutes the programmer recommends a value for AV delay and other delay parameters. The clinician can then act on the recommended value for AV delay by either using the suggested setting or modifying the suggesting setting in some way. The commanded optimization process can be performed when the patient in the presence of a programmer and a clinician, such as when the patient visits the clinician's office.

However, both physicians and patients benefit from a device solution capable of automatically optimizing CRM parameters without the inconvenience of a clinic visit. As the heart and the electrical activation times change over time for a patient, the optimal timing parameters will change. An ambulatory implementation of the pace timing optimization module addresses this need, where the data gathering, AV delay recommendation and parameter change could take place away from the clinic, while the patient is going about their normal life. The term "ambulatory" is used to mean herein that the process takes place when the patient is not in a clinical or hospital setting, but rather can take place when the patient is at home, walking around or the like. During the ambulatory optimization process, the CRM device will periodically gather data from the patient, determine an optimum or recommended AV delay value, and if certain system constraints are satisfied, modify the programmed AV delay value.

The AV delay value is just one example of a delay value and a programmable parameter, and refers to the atrio-ventricular delay, which is how long after a sensed or paced atrial contraction the device will wait before delivering a ventricular pacing pulse. In one embodiment, the range of values for AV delay is 40 milliseconds to 400 milliseconds, or 40 milliseconds to 300 milliseconds.

In many CRM systems, it is possible to program other types of pacing delays between two sites within the heart besides the AV delay. Examples of other types of delays that are relevant to programming a CRM system are the conduction time and pacing delay between the right atrium and right ventricle (RA-RV delay), the conduction time and pacing delay between the left atrium and left ventricle (LA-LV delay), between the right ventricle RV and the left ventricle LV (V-V delay), between RA and LA (RA-LA delay) if the LA requires pacing, between RA and LV, and between two different sites within a particular chamber. In some embodiments of a CRM system, optimal values for these other delay values can be suggested by a pace timing optimization module.

Figure 3:
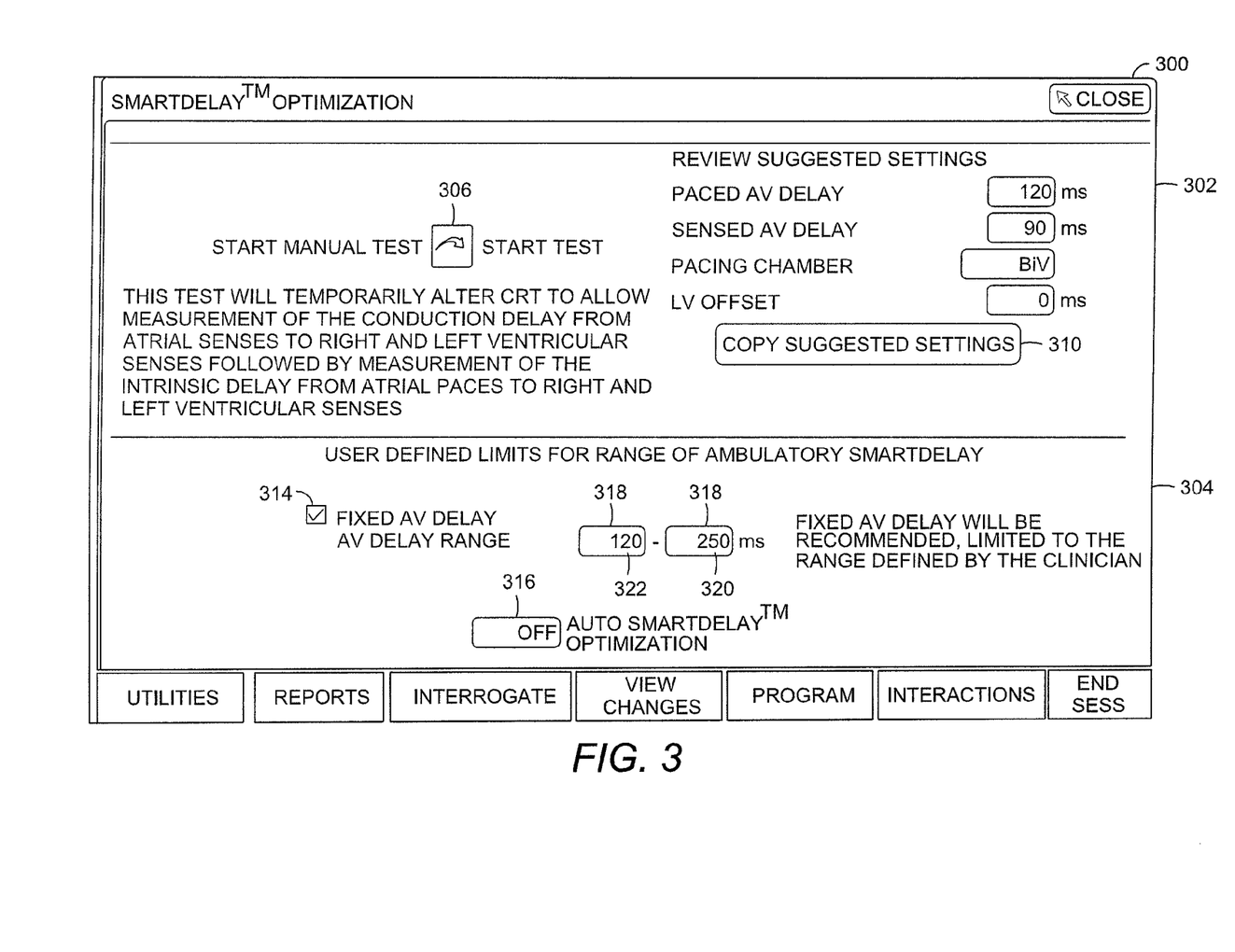
FIG. 3 is a schematic illustration of one example of a user interface screen for managing an optimization system of a cardiac rhythm management device that includes methods for managing both commanded optimizations and ambulatory optimizations.

Again referring to FIG. 2, in one embodiment of a CRM system the pace timing optimization feature can be accessed through the Brady and normal settings screen 140 by selecting the optimization button 142, which in this example is titled SmartDelay™ Optimization. Then, the user interface screen 300 of FIG. 3 is presented to the user which allows device parameters to be selected or verified by the user for the pace timing optimization process. The screen 300 includes fields for interacting with the commanded optimization process in the top part 302 and fields for the ambulatory optimization process in the bottom part 304.

The top part 302 includes a start test button 306 which will cause the CRM device to temporarily alter the cardiac resynchronization therapy settings to allow measurement of the conduction delay from atrial senses to right and left ventricular senses followed by measurement of the intrinsic delay from atrial paces to right and left ventricular senses. These measurements will allow the system to make recommendations for delay value settings. The top part 302 also includes fields for the system to present recommended suggested settings to the user for paced AV delay, sensed AV delay, the pacing chamber mode and the left ventricular (LV) offset. The top part also includes a copy suggested settings button 310 to allow the user to program or implement the suggested settings.

The bottom part 304 of the optimization module screen 300 is for the ambulatory optimization process and presents to the user several programmable parameters that are to be used as limits on the changes that can be made to the programmed AV delay by the ambulatory optimization process.

The recommendations for AV delay depend upon selection of maintaining fixed AV delay or using dynamic AV delay. If dynamic AV delay is selected, then the AV delay will vary with a sensed parameter, such as heart rate. For example, an increase in heart rate will cause a decrease in the AV delay, in one embodiment. In another embodiment, an increase in heart rate will cause a decrease in AV delay. If fixed AV delay is selected, then the AV delay will remain the same for a period of time in between optimization procedures, regardless of fluctuations in sensed parameters.

The selection between fixed AV delay and dynamic AV delay could be made in a number of different ways. In one embodiment, the determination is made in the CRM system and is not displayed to the user, but cannot be changed by the user. In another embodiment, the selection is made in the CRM system before programming, and is displayed to the user but cannot be changed by the user. In yet another embodiment, the selection is made in the CRM system before programming, is displayed to the user, and can be modified by the user. In another embodiment, the determination of a fixed AV delay or dynamic AV delay is determined by the programmer based on how other programming parameters are selected by the user. In one embodiment where the user can select between fixed AV delay and dynamic AV delay, a field 314 is provided to allow the user to indicate that the user prefers fixed AV delay. In the screen 300 of FIG. 3, the field 314 is checked indicating that fixed AV delay will be used. In some embodiments, the choice of fixed or dynamic AV delay is available in one or more different interface screens instead of or in addition to being present in screen 300.

In one embodiment, a button 316 is provided to allow the user to enable the ambulatory optimization module. Frequency of optimization is programmed via this parameter. In one embodiment, the user clicks on the button 316, and is then presented with a list of frequency options. In one embodiment, frequency options include off, daily, weekly, monthly, quarterly and yearly. A frequency setting can be stored by the device without any user input, and so the button 316 has options such as off and on, or disable and enable in that embodiment. In one embodiment, the user is allowed to overwrite the stored initial frequency setting. One option for an initial frequency setting is quarterly or monthly, along with a weekly or daily measurement that is stored for trending purposes. Measurements for trending purposes are further discussed herein.

Fields 318 are provided for entering the user-set AV delay range, which includes a user-set maximum AV delay 320 and a user-set minimum AV delay 322. The user-set AV delay range 318 places limits on the AV delay that will be programmed or implemented by the optimization module.

The optimization features discussed herein are complex, so in order to improve the ease of programming for the user, care is taken to avoid presenting programming options for the ambulatory optimization module to the user that are not allowed by the parameter interaction constraints. The system includes a seeding module which calculates initial seed values for the user-set delay range. These initial seed values will be present in fields 318 for delay values so that the user is initially presented with one viable option for the programming parameters. In one embodiment, the seeding module generates seed values for the user-set delay range so that the seed values do not violate any parameter interaction constraints and so that the seed values maximize the difference between ends of the user-set delay range.

In one embodiment, the seeding module generates the seed value for the user-set maximum delay value field 320 by ensuring that the following parameter constraint is satisfied: User-set Maximum AV delay+Min PVARP≤MTR.

Figure 4:
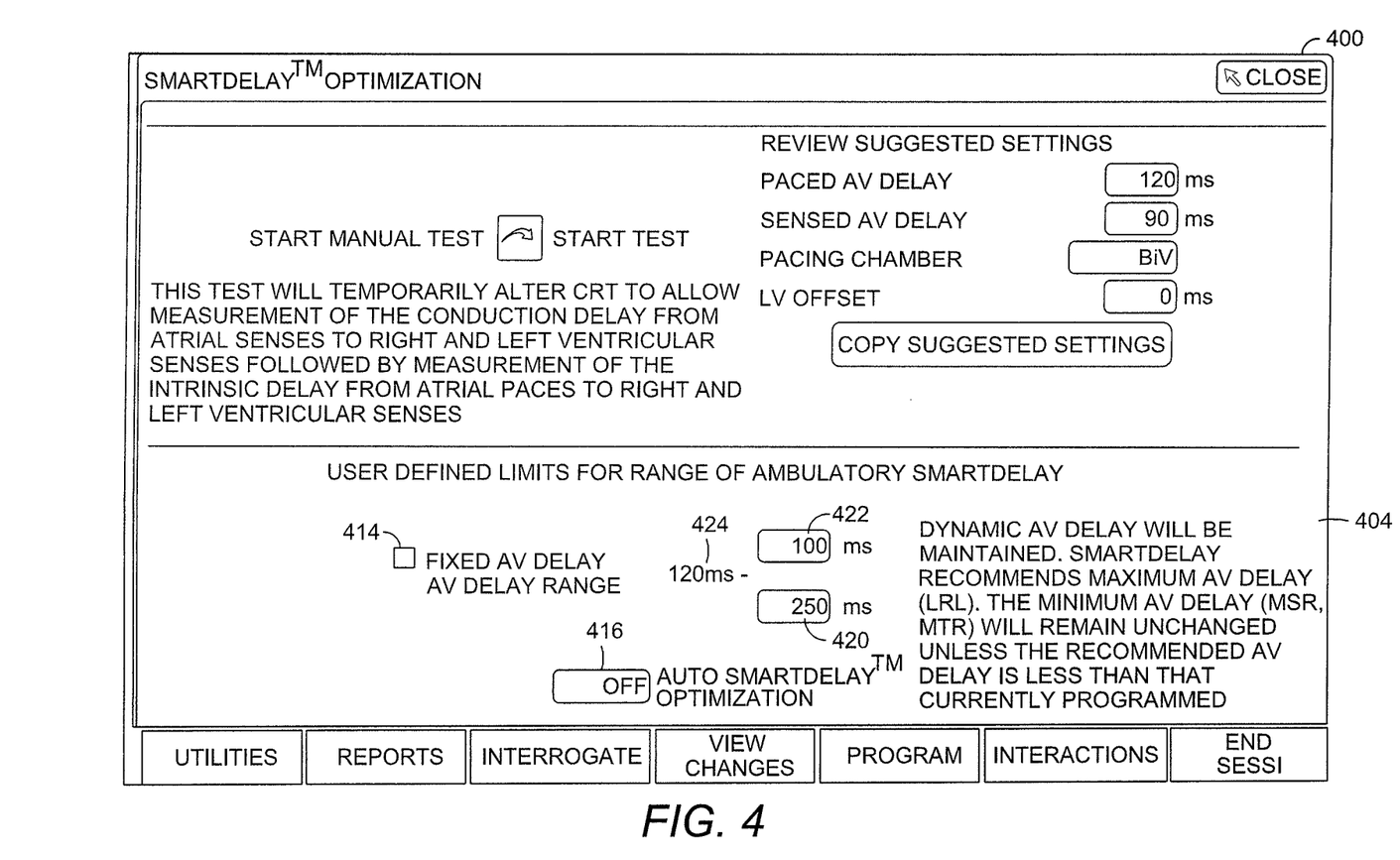
FIG. 4 is a schematic illustration of another example of a user interface screen for managing an optimization system of a cardiac rhythm management device that includes methods for managing both commanded optimizations and ambulatory optimizations.

FIG. 4 shows a screen 400 for programming the pace timing optimization module which is similar to screen 300 of FIG. 3 and where the bottom part 404 relates to ambulatory pace timing optimization. In screen 400 of FIG. 4, the fixed AV delay field 414 is unchecked, so that a dynamic AV delay will be maintained. Frequency button 416 is used to turn on the ambulatory pace timing optimization module and to set the frequency of the optimization process, as discussed with relation to FIG. 3. Screen 400 includes field 420 for the low end of a user-set maximum AV delay and field 422 for the high end of a user-set maximum AV delay. The minimum AV delay 424, in this case 120 milliseconds, will remain unchanged from what was programmed by the user for the paced AV delay or sensed AV delay in the Brady and normal settings screen 200, unless the AV delay that is recommended by the pace timing optimization module is less than the currently programmed value for those parameters.

Users are sometimes concerned that an ambulatory pace timing optimization module will cause changes in delay values that are too abrupt. In one embodiment, the system stores a change constraint for limiting changes in the delay value during a time period. For example, the change constraint for AV delay may be 20 milliseconds, 30 milliseconds, 40 milliseconds, 50 milliseconds, or another amount. In one embodiment, the change constraint is stored by the system without user input. In another embodiment, the change constraint is set by the clinician.

In one embodiment, the system stores two change constraints that are capable of having different values: an increment change constraint that restricts upward changes in the delay value and a decrement change constraint that restricts downward changes in the delay value. In one example, an increment change constraint of 40 milliseconds is set and a decrement change constraint of 10 milliseconds is set. In this case, the delay value can be increased by 40 milliseconds or less and can be decreased by 10 milliseconds or less at a single optimization session.

In some embodiments, the change in the programmed delay value is limited in further ways. In one embodiment, if the recommended delay value is very close to the current programmed delay value, such as small percentage or amount of the current programmed delay value, then no change is made to the current programmed delay value. For example, if the recommended delay value was within 3% of the programmed delay value, then no change would be made.

Figure 5:
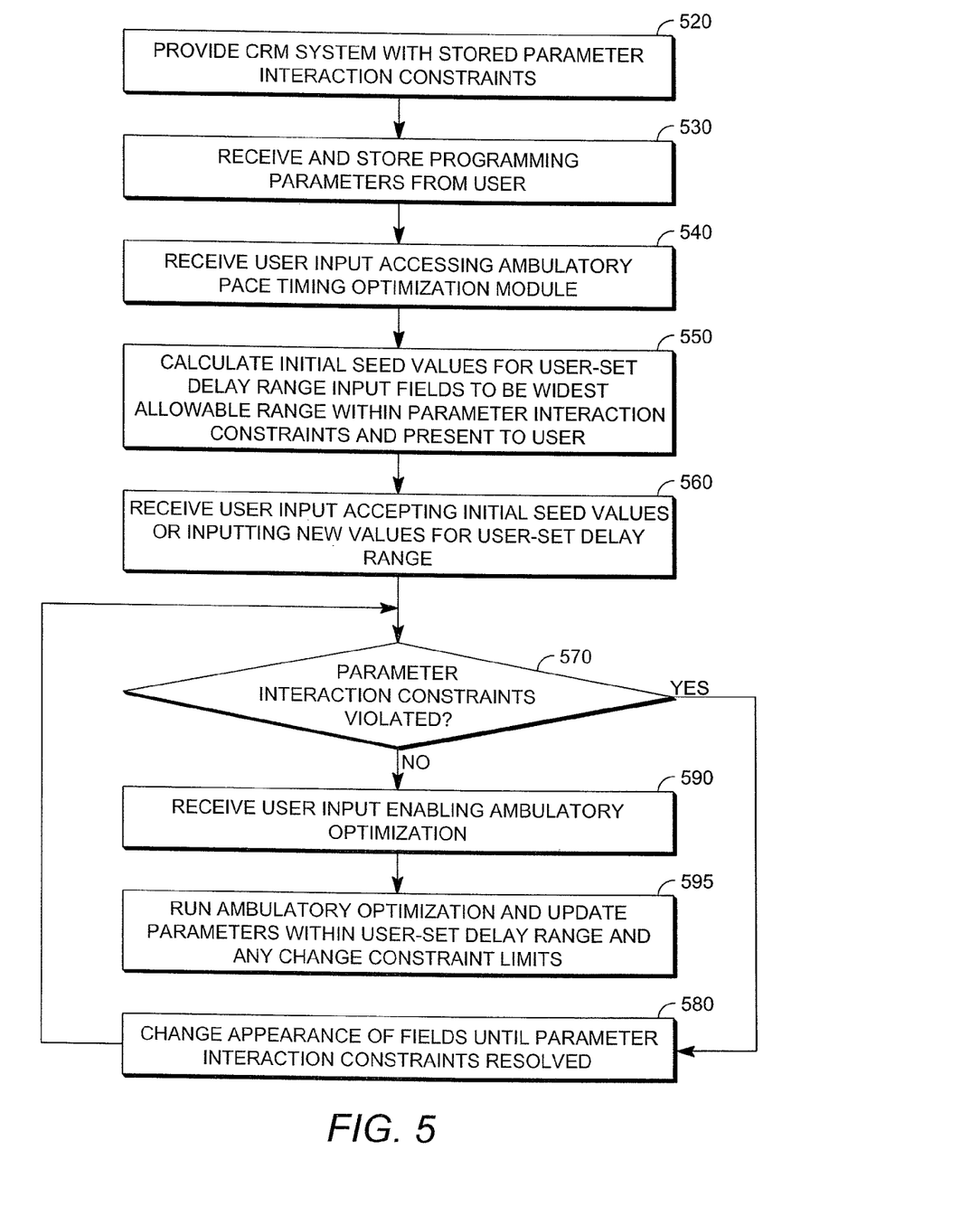
FIG. 5 is a flowchart illustrating the steps of one embodiment of a method for programming an ambulatory optimization system for cardiac rhythm management.

FIG. 5 illustrates one method of interacting with a user while programming a CRM system to use an ambulatory pace timing optimization module. Providing a CRM system having stored parameter interaction constraints is a first step 520. The CRM system uses a user display device and a user input device of a programmer to receive and store programming parameters from a user at step 530. Next, the user accesses the ambulatory pace timing optimization module at step 540. This can be accomplished by activating the optimization button 142 on screen 140 as shown in FIG. 2 in one embodiment. There are also many other techniques possible for accessing the ambulatory optimization module. Again referring to FIG. 5, the system calculates initial seed values for the user-set delay range input fields and then presents those to the user at step 550. The initial seed values for the user-set delay range will be calculated so that they do not violate any parameter interaction constraints and so that they maximize the difference between the ends of the user-set delay range. At step 560, the user is then given the opportunity to either accept the initial seed values, such as by closing the optimization window, or to overwrite the initial seed values by inputting new delay range values. When the user overwrites the initial seed values, there is the possibility that the new values will violate a parameter interaction constraint, which is examined by the system at step 570. If a parameter interaction constraint is violated, the appearance of the field is altered to draw the user's attention to that issue at step 580. For example, a background color or hash marks can be present in the field, or the border of the field can change to a different color. When there are no violations of parameter interaction constraints, the system can receive input enabling the ambulatory optimization module at step 590. The system then runs the ambulatory optimization at step 595, generating optimum delay values, also referred to as recommended delay values or suggested delay values. Those optimum delay values are then updated within the CRM system to become the programmed delay values.

However, if the system is programmed to store change constraint limits then the delay values are not changed by more than the applicable change constraint limit.

A delay value that is recommended by the optimization module does not always become the programmed delay value. The user-set delay range is a constraint on the programmed delay value, so that if the recommended delay value is outside of the user-set delay range, then the recommended delay value will not become the programmed delay value. Instead the end of the user-set delay range closest to the recommended delay value will become the programmed delay value. In one embodiment, the change constraint will also limit the programmed delay value as discussed herein.

In addition, there are other reasons that the recommended delay value, once calculated, may not become the programmed delay value. For example, if the patient experiences or has recently experienced an arrhythmia episode, the system can be programmed not to allow a change in the delay value. In one embodiment, the CRM system stores the recommended delay value each time that value is determined, and also stores the programmed delay value at each of those times. In one embodiment, the system is programmed to calculate the recommended delay value and store it without attempting to program the recommended delay value at certain time intervals. A system may more frequently calculate a recommended delay value than it attempts to program the value.

Figure 6:
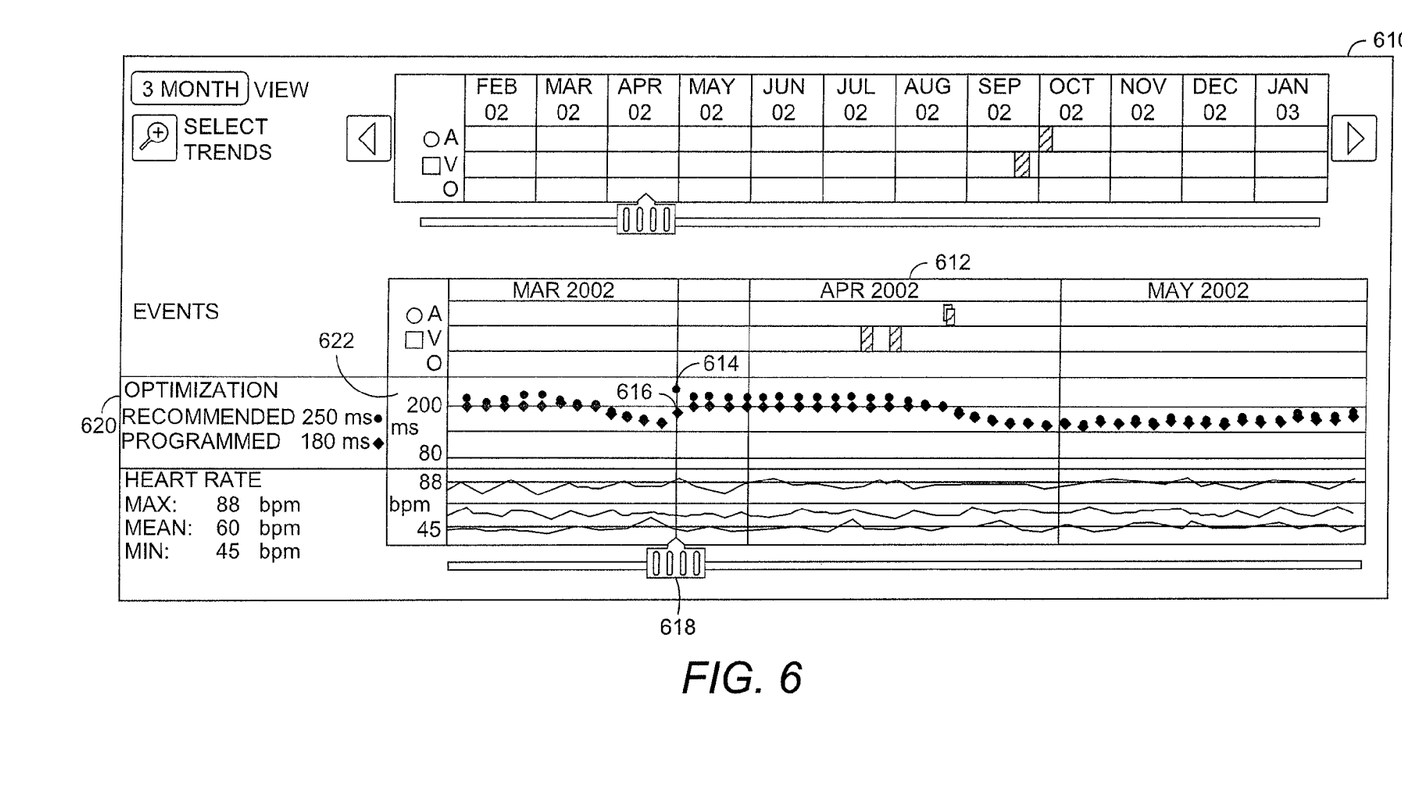
FIG. 6 is a schematic illustration of another example of a user interface screen for displaying programmed and recommended delay values for a cardiac rhythm management device.

In one embodiment, the CRM system is configured to display for a user a record of recommended delay values and programmed delay values at different points in time. FIG. 6 shows screen 610 which is one example of such a display.

A screen 610 show a graphic time line display 612 and includes recommended delay value data points 614 and programmed delay value data points 616 shown on a time line graph. A slide bar 618 is also provided in order to assist the user with getting more detailed information about any particular time point. The slide bar can be dragged into different locations along the time line by the user with user input devices. In one embodiment, when the slide bar line is positioned over a particular data point, the optimization text box 620 displays the recommended and programmed delay value for that point in time, and can also be configured to provide additional information about that point in time. In the example of FIG. 6, at the selected time point, the recommended AV delay was 250 milliseconds and the programmed AV delay was 180 milliseconds. The reason why the programmed value of 180 milliseconds at this point in time is not at the maximum user-set value of 200 milliseconds is because the programmed value is also restricted by a change constraint compared to the previous programmed value.

In one embodiment, the graphic time line display 612 also includes a user-set information text box 622 showing the maximum user-set delay range, which is 200 milliseconds in the example of FIG. 6, and the minimum user-set delay range, which is 80 milliseconds in the example.

There are many different ways to display historical recommended and programmed delay values to a user, and FIG. 6 illustrates just one of those ways. Further information is included in other embodiments such as one or more of frequency of optimization, distinctions between ambulatory and commanded recommendations, and distinctions between manual programmed changes and ambulatory programmed changes. Delay values for V-V delay could also be displayed in graphic display 612 or in a different display, as could the type of recommendation as biventricular, right ventricular or left ventricular.

One option for frequency programming is that there will be an attempt to re-program the delay value at one interval, such as weekly, and there will be a determination of a recommended delay value without an attempt to program the delay value at a second interval, such as daily. The determinations of recommended delay values can be stored and displayed to the user as shown in FIG. 6.

Some examples of parameter interaction constraints in one embodiment will now be listed. Additional parameter interaction constraints are present in one embodiment of a CRM system, but this list provides some specific examples of parameter interaction constraints that are stored by the programmer or external interface device.

Atrial tracking is maintained at the upper rate limit, so that this constraint is satisfied if the Minimum AV Delay Interval plus the Minimum Dynamic PVARP Interval is less than or equal to the Maximum Tracking Rate Interval. Atrial tracking is maintained at the lower rate limit, so that this constraint is satisfied if the Maximum AV Delay Interval plus the Maximum Dynamic PVARP Interval is less than or equal to the Lower Rate Limit Interval. A minimum 50 millisecond V-A timing is maintained, so that this constraint is satisfied if the Minimum AV Delay Interval plus 50 milliseconds is less than or equal to the Maximum Pacing Rate Interval. An alert is triggered when the V-A interval allows atrial pacing faster than the lowest tachy zone interval, so that this constraint is satisfied if the lowest VTachy Zone Interval is less than the Lower Rate Limit Interval minus the Maximum AV Delay Interval. A minimum 90 millisecond atrial sensing window is maintained, so that this constraint is satisfied when the following three conditions are all met: 1.) biventricular pacing is programmed, 2.) the absolute value of the LV offset is greater than or equal to 60 milliseconds, and 3.) atrial pace refractory period plus atrial cross-chamber RV pace refractory plus atrial cross-chamber LV pace refractory plus 90 milliseconds is less than or equal to the upper rate limit interval. User-set minimum AV delay is smaller than user-set maximum AV delay. User-set minimum AV delay is at least 30 milliseconds. User-set maximum AV delay is at least 300 milliseconds. Sensed AV delay is no longer than the paced AV delay. Sensed AV delay is within 100 milliseconds of paced AV delay.

This list is far from exhaustive, but these examples may improve understanding of the system.

One embodiment of a CRM device will now be described in more detail with reference to FIG. 1, which is a schematic of an exemplary CRM system 100. The system 100 can include an implantable medical device 114 disposed within a patient 112. The implantable medical device 114 can include pacing functionality. The implantable medical device 114 can be of various types such as, for example, a pacemaker, a cardioverter-defibrillator, a cardiac resynchronization device, a heart rhythm monitoring device, or the like. In some embodiments, the implantable medical device 114 can include one or more leads 122 disposed in or near the patient's heart 126.

The implantable medical device 114 can be in communication with a programmer 116. In some embodiments, communication between the implantable medical device 114 and the programmer 116 can be via inductive communication through a wand 110 held on the outside of the patient 112 near the implantable medical device 114. However, in other embodiments, communication can be carried out via radiofrequency transmission, acoustically, or the like.

The implantable medical device 114 can include one or more implantable sensors in order to gather data regarding the patient 112. For example, the implantable medical device 114 can include an activity level sensor, a respiration sensor, a blood pressure sensor, an impedance sensor, or other sensors.

The implantable medical device 114 can be configured to store data over a period of time, and periodically communicate with the programmer 116 or programmer 116 in order to transmit some or all of the stored data.

The programmer 116 can be for example, a programmer, a programmer/recorder/monitor device, a computer, a patient management system, a personal digital assistant (PDA), or the like. As used herein, the term programmer refers to a device that programs implanted devices, records data from implanted devices, and allows monitoring of the implanted device. Exemplary programmer/recorder/monitor devices include the Model 3120 Programmer, available from Boston Scientific Corporation, Natick, Mass. The programmer 116 can include a user input device, such as a keyboard 120 and/or a mouse 128. The programmer 116 can include a video output channel and video output device, such as a video display 118 for displaying video output. The displayed video output can include a user interface screen. In addition, the video display 118 can also be equipped with a touch screen, making it into a user input device as well.

The external interface device 116 can display real-time data and/or stored data graphically, such as in charts or graphs, and textually through the user interface screen. In addition, the external interface device 116 can present textual information to a user along with several response options. The external interface device 116 can also input and store a user's response to a question, and can store a user's text response in some embodiments.

In one embodiment, the external interface device 116, which can also be referred to as a user interface, is in communication with a patient management computer system 132. The communication link between the user interface 116 and the patient management computer system 132 may be via phone lines, the Internet 130, or any other data connection. The user interface 116 can also be used when it is not in communication with a device, but is only in communication with the patient management computer system 132.

In one embodiment, the external interface device 116 is capable of changing the operational parameters of the implantable medical device 114, and is therefore referred to as a programmer. Typically, programmers are used to interface with CRM devices in a clinic or hospital setting. In this context, the user of the external interface device is a physician or trained technician.

Figure 7:
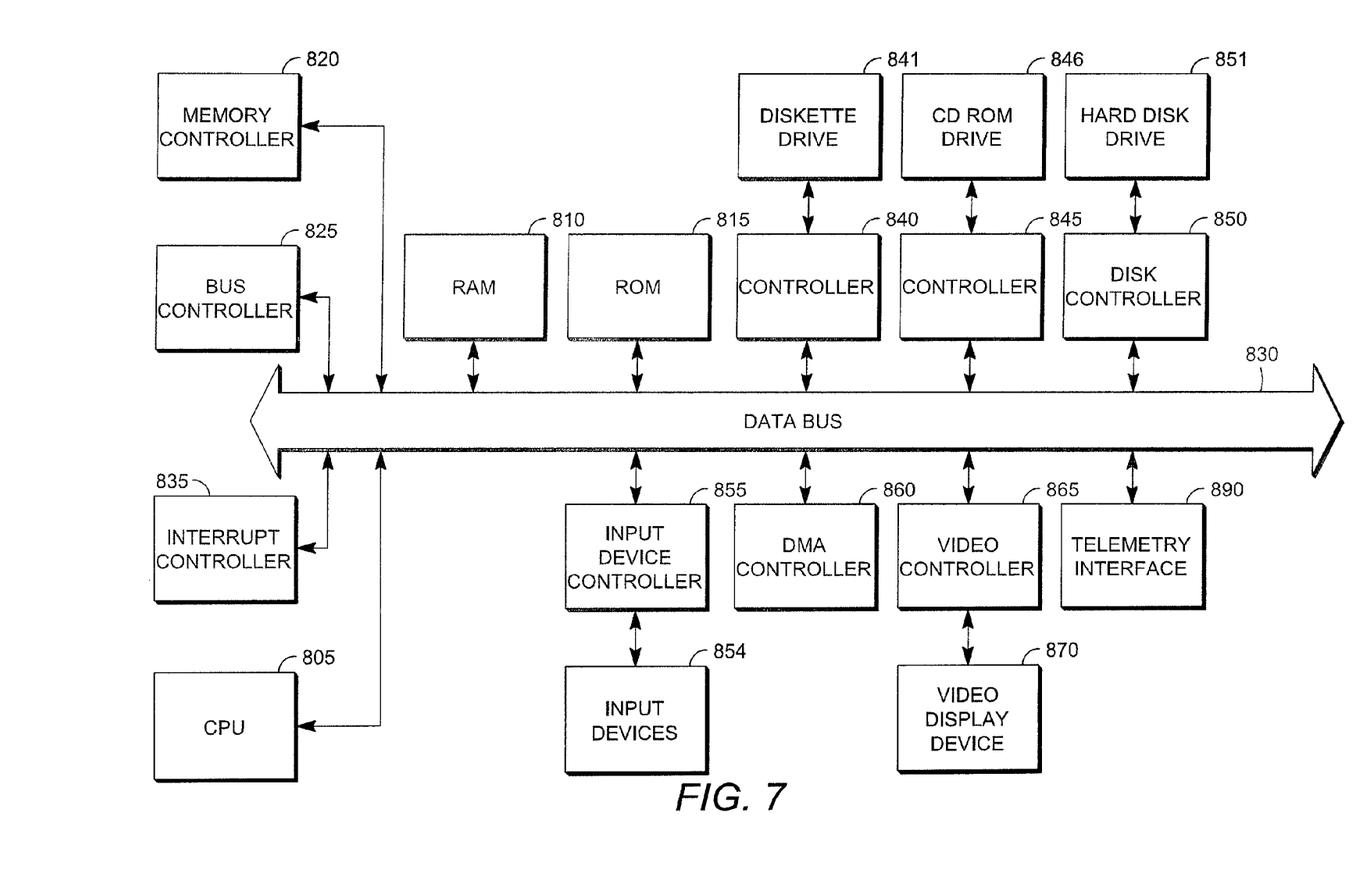
FIG. 7 is a schematic diagram of an implementation of the components of an external interface device such as a programmer, in accordance with various embodiments.

Programmers 116 can include components common to many computing devices. User interface devices 516 to display and received information from users can also include components common to many computing devices. Referring now to FIG. 7, a diagram of various components is shown in accordance with some embodiments of the invention. However, it is not required that an external interface device or programmer have all of the components illustrated in FIG. 8.

In one embodiment, the external interface device includes a central processing unit (CPU) 805 or processor, which may include a conventional microprocessor, random access memory (RAM) 810 for temporary storage of information, and read only memory (ROM) 815 for permanent storage of information. A memory controller 820 is provided for controlling system RAM 810. A bus controller 825 is provided for controlling data bus 830, and an interrupt controller 835 is used for receiving and processing various interrupt signals from the other system components.

Mass storage can be provided by diskette drive 841, which is connected to bus 830 by controller 840, CD-ROM drive 846, which is connected to bus 830 by controller 845, and hard disk drive 851, which is connected to bus 830 by controller 850. User input to the programmer system may be provided by a number of devices. For example, input devices 854 such as a keyboard and mouse can connect to bus 830 by input device controller 855. DMA controller 860 is provided for performing direct memory access to system RAM 810. A visual display is generated by a video controller 865 or video output, which controls video display 870. The external system can also include a telemetry interface 890 or telemetry circuit which allows the external system to interface and exchange data with an implantable medical device. It will be appreciated that some embodiments may lack various elements illustrated in FIG. 7.

A seeding module, parameter interaction module, pace timing optimization module and combinations thereof can be present in the programmer in different embodiments.

Figure 8:
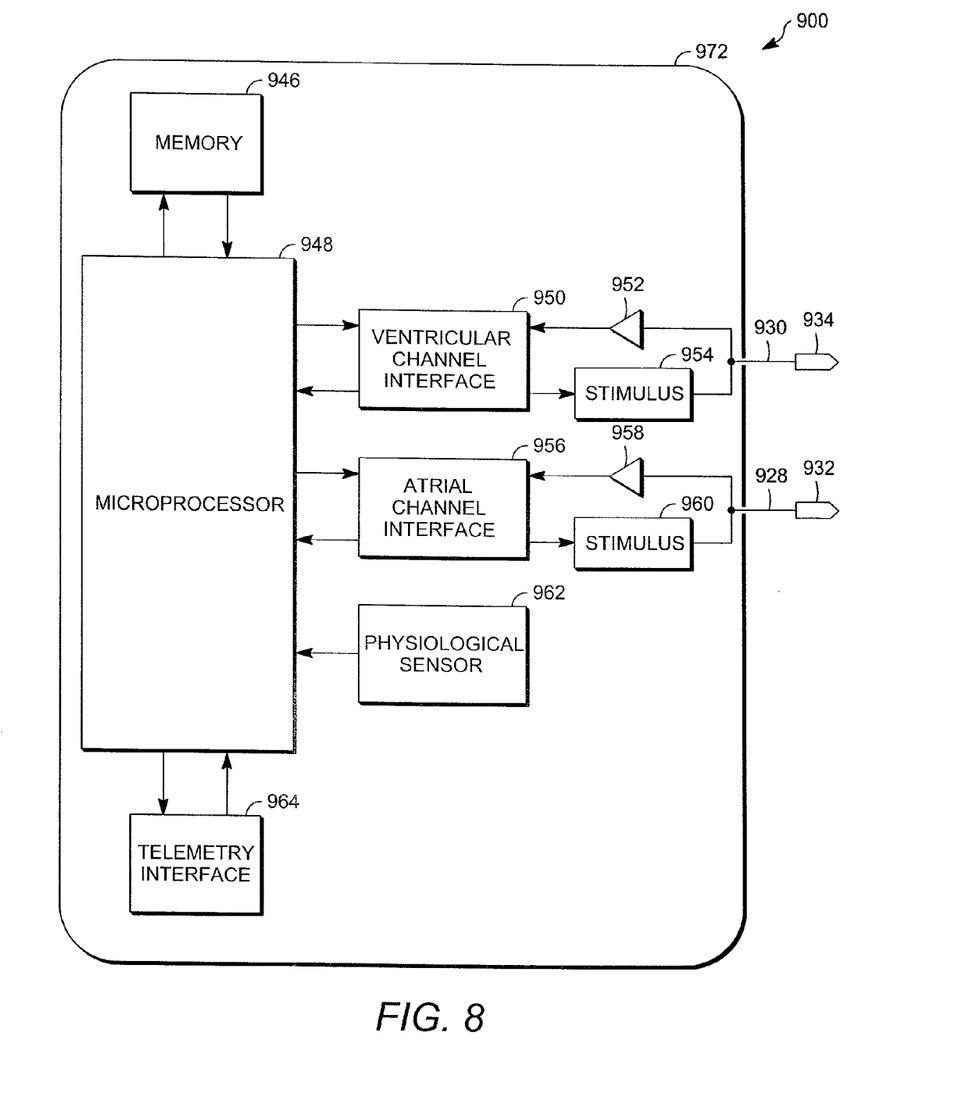
FIG. 8 is a schematic view of components of one example of an implantable device in accordance with an embodiment of the invention.

Referring now to FIG. 8, some components of an exemplary implantable system 900 are schematically illustrated. The implantable medical system 900 can include an implantable medical device 972 coupled to one or more stimulation leads 930 and 928. The implantable device 972 can also include one or more physiological sensors 962, or other sensors, such as a pressure sensor, impedance sensor and others.

The implantable device can include a microprocessor 948 (or processor) that communicates with a memory 946 via a bidirectional data bus. The memory 946 typically comprises ROM or RAM for program storage and RAM for data storage. The implantable device can be configured to execute various operations such as processing of signals and execution of methods as described herein. A telemetry interface 964 is also provided for communicating with an external unit, such as a programmer device or a patient management system.

The implantable device can include ventricular sensing and pacing channels comprising sensing amplifier 952, output circuit 954, and a ventricular channel interface 950 which communicates bi-directionally with a port of microprocessor 948. The ventricular sensing and pacing channel can be in communication with stimulation lead 930 and electrode 934. The implantable device can include atrial sensing and pacing channels comprising sensing amplifier 958, output circuit 960, and an atrial channel interface 956 which communicates bi-directionally with a port of microprocessor 948. The atrial sensing and pacing channel can be in communication with stimulation lead 928 and electrode 932. For each channel, the same lead and electrode can be used for both sensing and pacing. The channel interfaces 950 and 956 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

A seeding module, parameter interaction module, pace timing optimization module and combinations thereof can be present in the device in different embodiments.

Figure 9:
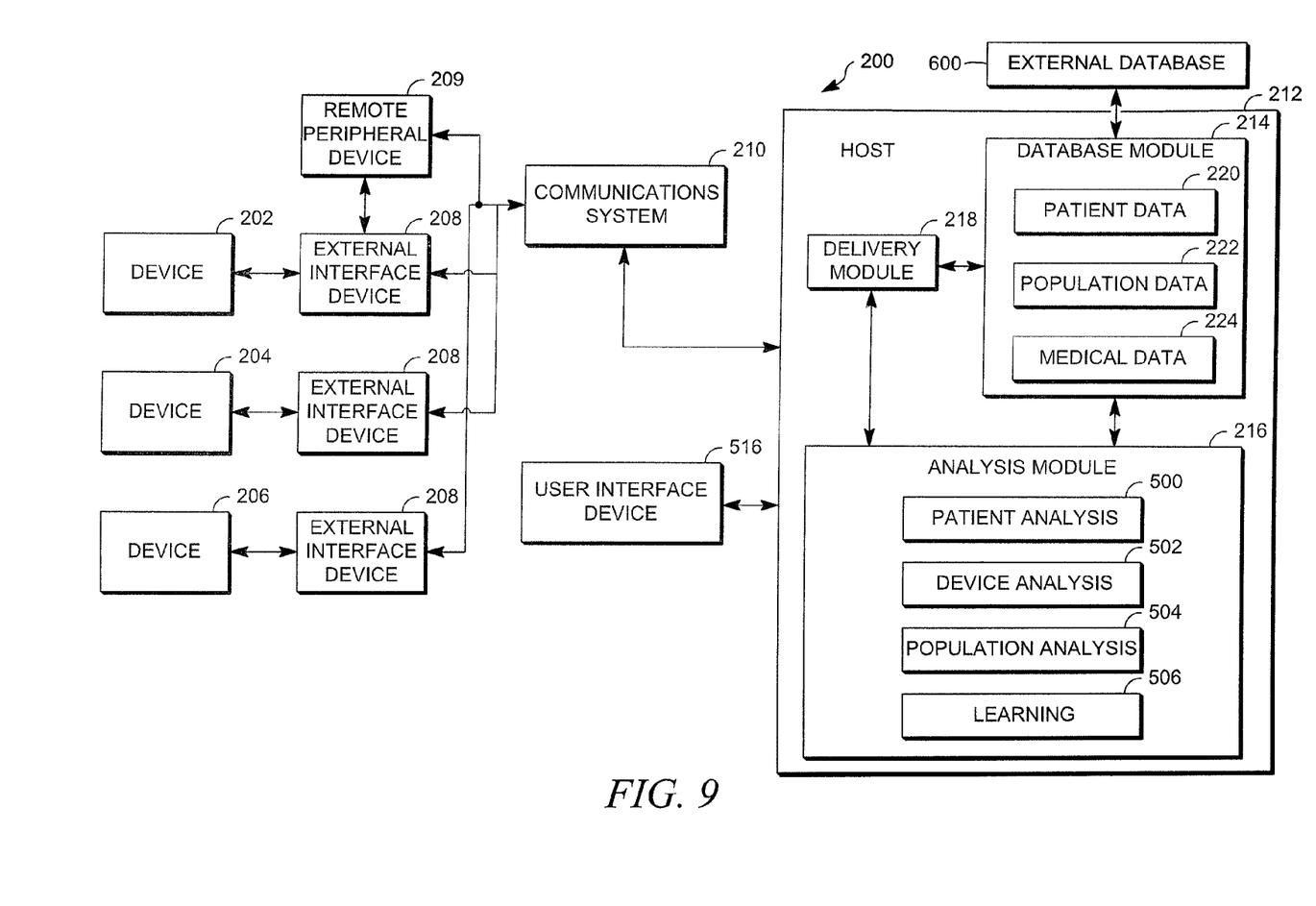
FIG. 9 is a schematic illustration of a patient management system consistent with at least one embodiment of the invention.

FIG. 9 is a schematic illustration of a patient management system consistent with at least one embodiment of the invention. The patient management system is capable of generating an episode database and supporting a training module. Patient management system 200 generally includes one or more devices 202, 204, and 206, one or more external interface devices 208, a communication system 210, one or more remote peripheral devices 209, and a host 212.

Each component of the patient management system 200 can communicate using the communication system 210. Some components may also communicate directly with one another. The various components of the example patient management system 200 illustrated herein are described below.

Data-generating devices 202, 204, and 206 can be implantable devices or external devices that may provide one or more of the following functions with respect to a patient: (1) sensing, (2) data analysis, and (3) therapy. For example, in one embodiment, devices 202, 204, and 206 are either implanted or external devices used to measure a variety of physiological, subjective, and environmental conditions of a patient using electrical, mechanical, and/or chemical means. The devices 202, 204, and 206 can be configured to automatically gather data or can require manual intervention by the patient or another person. The devices 202, 204, and 206 can be configured to store data related to the physiological and/or subjective measurements and/or transmit the data to the communication system 210 using a variety of methods, described in detail below. Although three devices 202, 204, and 206 are illustrated in the example embodiment shown, many more devices can be coupled to the patient management system. In one embodiment, each of the devices 202, 204 and 206 is serving a different patient. In one embodiment, two or more devices are serving a single patient.

The devices 202, 204, and 206 can be configured to analyze the measured data and act upon the analyzed data. For example, the devices 202, 204, and 206 can be configured to modify therapy or provide an alarm based on the analysis of the data.

In one embodiment, devices 202, 204, and 206 provide therapy. Therapy can be provided automatically or in response to an external communication. Devices 202, 204, and 206 are programmable in that the characteristics of their sensing, therapy (e.g., duration and interval), or communication can be altered by communication between the devices 202, 204, and 206 and other components of the patient management system 200. Devices 202, 204, and 206 can also perform self-checks or be interrogated by the communication system 210 to verify that the devices are functioning properly. Examples of different embodiments of the devices 202, 204, and 206 are provided herein.

Devices implanted within the body have the ability to sense and communicate as well as to provide therapy. Implantable devices can provide direct measurement of characteristics of the body, including, without limitation, electrical cardiac activity (e.g., a pacemaker, cardiac resynchronization management device, defibrillator, etc.), physical motion, temperature, heart rate, activity, blood pressure, breathing patterns, ejection fractions, blood viscosity, blood chemistry, blood glucose levels, and other patient-specific clinical physiological parameters, while minimizing the need for patient compliance. Derived measurements can also be determined from the implantable device sensors (e.g., a sleep sensor, functional capacity indicator, autonomic tone indicator, sleep quality indicator, cough indicator, anxiety indicator, and cardiovascular wellness indicator for calculating a quality of life indicator quantifying a patient's overall health and well-being).

Devices 202, 204, and 206 can also be external devices, or devices that are not implanted in the human body, that are used to measure physiological data (e.g., a thermometer, sphygmomanometer, or external devices used to measure blood characteristics, body weight, physical strength, mental acuity, diet, heart characteristics, and relative geographic position).

The patient management system 200 may also include one or more remote peripheral devices 209 (e.g., cellular telephones, pagers, PDA devices, facsimiles, remote computers, printers, video and/or audio devices) that use wired or wireless technologies to communicate with the communication system 210 and/or the host 212.

The example database module 214 includes a patient database 220, a population database 222, and a medical database 224, all of which are described further below. The patient database 220 includes patient specific data, including data acquired by the devices 202, 204, and 206, as well as a patient's medical records and historical information. The population database 222 includes non-patient specific data, such as data relating to other patients and population trends. The example medical database 224 includes clinical data relating to the treatment of diseases, such as historical trend data for multiple patients in the form of a record of progression of their disease(s) along with markers of key events.

Information can also be provided from an external source, such as external database 600. For example, the external database 600 includes external medical records maintained by a third party, such as drug prescription records maintained by a pharmacy, providing information regarding the type of drugs that have been prescribed for a patient or, in another example, authorization data from patient groups that have authorized users to view arrhythmia episode data.

The example analysis module 216 includes a patient analysis module 500, device analysis module 502, population analysis module 504, and a learning module 506. Patient analysis module 500 may utilize information collected by the patient management system 200, as well as information for other relevant sources, to analyze data related to a patient and provide timely and predictive assessments of the patient's well-being. Device analysis module 502 analyzes data from the devices 202, 204, and 206 and external interface devices 208 to predict and determine device issues or failures. Population analysis module 504 uses the data collected in the database module 214 to manage the health of a population. Learning module 506 analyzes the data provided from the various information sources, including the data collected by the patient system 200 and external information sources, and may be implemented via a neural network (or equivalent) system to perform, for example, probabilistic calculations.

One or more portions of the analysis module 216, such as the population analysis module 504, may be located remotely from other parts of the patient management system 200.

Delivery module 218 coordinates the delivery of reports, patient alerts or programming recommendations based on the analysis performed by the host 212. For example, based on the data collected from the devices and analyzed by the host 212, the delivery module 218 can deliver information to the caregiver, user, or to the patient using, for example, a display provided on the external interface device 208. A user interface device 516 that is independent of a data-generating device may also be used to deliver information. The external interface device 208 and user interface device 516 are also configured, according to multiple embodiments, to display a report, alert, or programming recommendation, and receive other data from the user. Displayed data, as described above, can be determined by the delivery module 218.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed:

1. A cardiac rhythm management system including a programmable cardiac rhythm management device having data collection devices for collecting ambulatory patient data, the system comprising:
   a. a programming parameter module for storing programmable parameters for the device, wherein each parameter has a predefined set of possible values, wherein one programmable parameter is a delay value;
   b. an optimization module adapted to optimize pace timing and determine a recommended delay value based on the ambulatory patient data, wherein the optimization module is configured to store one or more change constraints that restrict an amount of increment and decrement changes in the programmed delay value during each optimization session;
   c. a parameter interaction module adapted for storing parameter interaction constraints between different programmable parameters;
   d. a user input device adapted to receive values from a user for a user-set delay range, wherein the user-set delay range provides outer limits of a programmed delay value, wherein the user input device is configured to allow the user to overwrite the one or more change constraints;
   e. a user display device adapted to present an input screen to the user, wherein the input screen comprises user-set delay range input fields; and
   f. a seeding module adapted to calculate initial seed values for the user-set delay range input fields, wherein the seed values do not violate any parameter interaction constraints and maximize the difference between ends of the user-set delay range;
   wherein the cardiac rhythm management device is configured to be implanted in a patient, wherein the patient data includes heart rate and at least a portion of an intracardiac electrogram, wherein the data collection devices include one or more electrodes, and wherein the cardiac rhythm management device is configured to provide therapy to a patient by delivering electrical stimuli to the patient via the one or more electrodes, wherein the electrical stimuli is delivered to the patient in a manner determined by the programmable parameters.

2. The system of claim 1 wherein the user input device is further adapted to receive user input overwriting the seed values for the user-set delay range.

3. The system of claim 2 wherein if overwritten values for user-set delay range violate parameter interaction constraints, then the appearance of the user-set delay range input fields is the appearance is modified.

4. The system of claim 1, wherein the user set delay range comprises a user-set maximum delay and a user-set minimum delay and wherein:
   a. a seed value for the user-set maximum delay is the highest of the predefined set of possible values that does not violate any parameter interaction constraints;
   b. a seed value for the user-set minimum delay is the lowest of the predefined set of possible values that does not violate any parameter interaction constraints.

5. The system of claim 1 wherein the optimization module is configured to store the recommended delay value and the programmed delay value each time it is determined.

6. The system of claim 1 wherein the user input device is further adapted to receive user input turning on and turning off the pace timing optimization module.

7. The system of claim 1 wherein the delay value is selected from the group comprising A-V delay, V-V delay, LA-LV delay, RA-RV delay, RA-LA delay, and RA-LV delay, and the delay between two pacing sites within a chamber.

8. A method for cardiac rhythm management using a programmable cardiac rhythm management device, the method comprising:
   a. storing parameter interaction constraints between different programmable parameters,
   b. storing programmable parameters for the device, wherein each programmable parameter has a predefined set of possible values, wherein one programmable parameter is a delay value;
   c. storing one or more change constraints that restrict an amount of increment and decrement changes in the programmed delay value during each optimization session;
   d. calculating initial seed values for user-set delay range input fields, wherein the seed values do not violate any parameter interaction constraints and maximize the difference between ends of the user-set delay range, wherein the user-set delay range provides the outer limits of a programmed delay value;
   e. presenting an input screen to the user on a user display device, wherein the input screen comprises user-set delay range input fields containing the initial seed values;
   f. receiving values from a user for the user-set delay range;
   g. receiving a value for the one or more change constraints from the user;
   h. collecting patient data including ambulatory patient data; and
   i. determining a recommended delay value based on the ambulatory patient data;
   wherein the cardiac rhythm management device is configured to be implanted in a patient, where the patient data includes heart rate and at least a portion of an intracardiac electrogram, wherein the data collection devices include one or more electrodes, and wherein the cardiac rhythm management device is configured to provide therapy to a patient by delivering electrical stimuli to the patient via the one or more electrodes, wherein the electrical stimuli is delivered to the patient in a manner determined by the programmable parameters.

9. The method of claim 8 further comprising receiving user input overwriting the seed values for the user-set delay range.

10. The method of claim 9 further comprising if overwritten values for user-set delay range violate parameter interaction constraints, then modifying the appearance of the user-set delay range input fields.

11. The system of claim 8 further comprising each time the recommended delay value is determined, storing the recommended delay value and the programmed delay value.

12. The system of claim 11 further comprising displaying for a user a record of recommended delay values and programmed delay values at different points in time.

13. The method of claim 8 further comprising receiving user input turning on and turning off the pace timing optimization module.

14. The method of claim 8 wherein the delay value is selected from the group comprising A-V delay, V-V delay, LA-LV delay, RA-RV delay, RA-LA delay, and RA-LV delay, and the delay between two pacing sites within a chamber.

15. A cardiac rhythm management system comprising:
   a. a programmable cardiac rhythm management (CRM) device, the CRM device comprising:
      i. data collection devices for collecting patient data including ambulatory patient data;
      ii. an ambulatory pace timing optimization module adapted to determine a recommended delay value based on the ambulatory patient data, wherein the optimization module is configured to store one or more change constraints that restrict an amount of increment and decrement changes in the programmed delay value during each optimization session; and
      iii. a programming parameter module for storing programmable parameters for the device wherein each parameter has a predefined set of possible values, wherein one programmable parameter is a delay value;
   wherein the cardiac rhythm management device is configured to be implanted in a patient, wherein the patient data includes heart rate and at least a portion of an intracardiac electrogram, wherein the data collection devices include one or more electrodes, and wherein the cardiac rhythm management device is configured to provide therapy to a patient by delivering electrical stimuli to the patient via the one or more electrodes, wherein the electrical stimuli is delivered to the patient in a manner determined by the programmable parameters; and
   b. an external programmer comprising control circuitry and a wireless communications module for sending instructions wirelessly to the CRM device, the programmer further comprising:
      i. a parameter interaction module for storing parameter interaction constraints between different programmable parameters,
      ii. a user input device adapted to receive values from a user for a user-set delay range, wherein the user-set delay range provides the outer limits of a programmed delay value, wherein the user set delay range comprises a user-set maximum delay and a user-set minimum delay, wherein the user input device is configured to allow the user to overwrite the one or more change constraints;

ii. a user display device adapted to present an input screen to the user, wherein the input screen comprises user-set delay range input fields; and
iv. a seeding module adapted to calculate initial seed values for the user-set delay range input fields, wherein:
 1. a seed value for the user-set maximum delay is the highest of the predefined set of possible values that does not violate any parameter interaction constraints;
 2. a seed value for the user-set minimum delay is the lowest of the predefined set of possible values that does not violate any parameter interaction constraints.

* * * * *